US004001674B2

United States Statutory Invention Registration [19]

[11] Reg. Number: H1674

Ames et al.

[45] Published: Aug. 5, 1997

[54] CONVERTIBLE BELTED DIAPER

[76] Inventors: Kathleen Quinlan Ames; Merlene Adams Cummins; Gayle Rose Bushman, all of 6100 Center Hill Rd., Cincinnati, Ohio 45224

[21] Appl. No.: 384,201

[22] Filed: Feb. 3, 1995

Related U.S. Application Data

[63] Continuation of Ser. No. 184,618, Jan. 19, 1994, abandoned.

[51] Int. Cl.[6] ..... A61F 13/15

[52] U.S. Cl. ..... 604/389; 604/385.1; 604/386; 604/396

[58] Field of Search ..... 604/385.1–387, 604/389, 396–402; 2/72, 76, 213, 226, 236, 919, 400, 402–403, 406, 408

[56] References Cited

U.S. PATENT DOCUMENTS

| | | | |
|---|---|---|---|
| 2,290,110 | 7/1942 | McGraw | 128/284 |
| 2,545,761 | 3/1951 | Brink | 128/287 |
| 2,607,348 | 8/1952 | Rosenblatt | 604/386 |
| 2,638,899 | 5/1953 | Ambarian | 128/284 |
| 2,739,595 | 3/1956 | Huggins | 604/327 |
| 2,841,147 | 7/1958 | McLaurin | 128/275 |
| 3,618,608 | 11/1971 | Brink | 128/287 |
| 3,882,871 | 5/1975 | Taniguchi | 604/391 |
| 4,024,867 | 5/1977 | Mesek | 128/287 |
| 4,051,854 | 10/1977 | Aaron | 604/394 |

(List continued on next page.)

FOREIGN PATENT DOCUMENTS

| | | | |
|---|---|---|---|
| 0 274 753 | 7/1988 | European Pat. Off. | A41B 13/02 |
| 0487788 | 6/1992 | European Pat. Off. | 604/398 |
| 0528282 | 2/1993 | European Pat. Off. | 604/396 |
| 0532034 | 3/1993 | European Pat. Off. | 604/392 |
| 2586588 | 3/1987 | France | 604/391 |
| 2606257 | 5/1988 | France | 604/356 |
| 2612770 | 9/1988 | France | A61F 13/00 |
| 1 491 234 | 4/1969 | Germany . | |
| 4259457 | 9/1992 | Japan | 604/389 |
| 1 516 287 | 7/1978 | United Kingdom | A41B 13/02 |
| 1526740 | 8/1978 | United Kingdom | 2/403 |

OTHER PUBLICATIONS

Translation of French Patent No. 2,606,251, 12 pgs.

*Primary Examiner*—Michael J. Carone
*Assistant Examiner*—Theresa M. Wesson

[57] ABSTRACT

An absorbent article such as a disposable diaper, incontinence brief, diaper holder, training pant or the like, having a fastening system that provides the user with different options as to how the absorbent article will be constructed and fitted to the wearer. The fastening system allows the wearer to choose between conventional, belted, and pull-up diaper configurations. Further, the fastening system is designed to ensure easy changing and removal of the absorbent article as well as easy inspection for soiling. Such absorbent articles comprise a containment assembly generally comprising a liquid pervious topsheet, a liquid impervious backsheet, an absorbent core disposed between the topsheet and the backsheet, first and second belt flaps extending laterally outwardly from opposite sides of the containment assembly, and a refastenable fastening system comprising a first fastening assembly and a second fastening assembly. The first fastening assembly is designed for constructing the absorbent article in a belted configuration. The second fastening assembly, designed as an alternative to the first fastening assembly, provides a system for fastening the absorbent article in a conventional configuration.

15 Claims, 8 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

U.S. PATENT DOCUMENTS

| | | | |
|---|---|---|---|
| 4,229,835 | 10/1980 | Shaw | 2/406 |
| 4,568,341 | 2/1986 | Mitchell et al. | 604/368 |
| 4,573,987 | 3/1986 | Lamb, Jr. | 604/378 |
| 4,617,022 | 10/1986 | Pigneul et al. | 604/391 |
| 4,771,483 | 9/1988 | Hooreman et al. | 2/237 |
| 4,773,900 | 9/1988 | Krushel | 604/391 |
| 4,846,815 | 7/1989 | Scripps | 604/391 |
| 4,869,724 | 9/1989 | Scripps | 604/389 |
| 4,906,243 | 3/1990 | Dravland | 604/394 |
| 4,909,802 | 3/1990 | Ahr et al. | 604/385.1 |
| 4,963,140 | 10/1990 | Robertson et al. | 604/389 |
| 4,964,860 | 10/1990 | Gipson et al. | 604/391 |
| 4,978,345 | 12/1990 | Holliday et al. | 604/384 |
| 4,988,346 | 1/1991 | Pfefferkorn | 604/389 |
| 5,019,065 | 5/1991 | Scripps | 604/385.1 |
| 5,031,248 | 7/1991 | Kemper | 2/400 |
| 5,032,122 | 7/1991 | Noel et al. | 604/391 |
| 5,069,678 | 12/1991 | Yamamoto et al. | 604/385.1 |
| 5,100,399 | 3/1992 | Janson et al. | 604/391 |
| 5,135,522 | 8/1992 | Fahrenkrug et al. | 604/385.1 |
| 5,143,679 | 9/1992 | Weber et al. | 264/288.8 |
| 5,151,092 | 9/1992 | Buell et al. | 604/385.2 |
| 5,156,793 | 10/1992 | Buell et al. | 264/288.8 |
| 5,167,897 | 12/1992 | Weber et al. | 264/288.8 |
| 5,187,817 | 2/1993 | Zolner | 2/400 |
| 5,196,000 | 3/1993 | Clear et al. . | |
| 5,209,743 | 5/1993 | Hardison | 604/391 |
| 5,246,433 | 9/1993 | Hasse et al. | 604/396 |
| 5,261,901 | 11/1993 | Guay | 604/391 |
| 5,295,986 | 3/1994 | Zehner et al. | 604/385.2 |
| 5,368,585 | 11/1994 | Dokken | 604/393 |

CONVERTIBLE BELTED DIAPER

This is a continuation of application Ser. No. 08/184,618, filed on Jan. 19, 1994, now abandoned.

FIELD OF INVENTION

The present invention relates to absorbent articles such as diapers, incontinence briefs, diaper holders, training pants and the like, and more particularly, to absorbent articles having a fastening system that provides the user with different options as to how the diaper will be constructed and fitted to the wearer.

BACKGROUND OF THE INVENTION

Infants and other incontinent individuals wear absorbent articles such as diapers to receive and contain urine and other body exudates. Absorbent articles function both to contain discharged materials and to isolate the materials from the body of the wearer and from the wearer's garments and bed clothing. Disposable absorbent articles having many different basic designs are known to the art. For example, U.S. Pat. No. Re. 26,152, entitled "Disposable Diaper" issued to Duncan and Baker on Jan. 31, 1967 describes a conventional disposable diaper which has achieved worldwide acceptance and commercial success. Further, U.S. Pat. No. 4,964,860 entitled "Detachable Two Piece Absorbent Garment" issued to Gipson et al. on Oct. 23, 1990 discloses a belted absorbent article. Finally, U.S. Pat. No. 5,246,433 entitled "Elasticized Disposable Training Pant And Method of Making The Same" issued to Hasse et al. on Sep. 21, 1993 discloses a unitary disposable absorbent article that can be used as a training pant. However, the absorbent articles currently available to the public fail to provide many of the benefits that could be achieved by absorbent articles having a fastening system that allows the user to choose the most desirable diaper configuration for each particular use.

In the market today, the consumer has a number of different basic diaper designs to choose from depending on the desired options, comfort and cost, including conventional diapers, belted diapers, and "pull-up" type training pants. Conventional diaper designs are generally the least expensive type of absorbent article to produce and are generally acceptable for use on small babies and persons who are sick or otherwise confined to a bed. A conventional diaper is fitted to the wearer by first placing a portion of the diaper under the wearer (generally, the back portion of the diaper is placed under the buttocks and rear waist of the wearer) and then pulling the remainder of the diaper through the wearer's legs. The rear portion of the diaper is then attached to the front portion of the diaper on each side of the wearer. However, such conventional configurations tend to be very difficult to use when the wearer refuses to remain still throughout the period of application. Further, adult wearers often find the conventional type absorbent articles difficult to put on themselves without assistance. Further, the conventional absorbent article configuration lacks an easy method for inspection without complete removal of the absorbent article.

Belted diapers have been introduced to overcome some of the problems with the conventional type diapers. Belted diapers are generally fitted to the wearer by positioning the diaper such that the belt can be fastened about the waist of the wearer with the remainder of the diaper hanging down between the legs of the wearer. The part of the diaper hanging down from the waist is then pulled through the legs of the wearer and attached to the belted part of the diaper near the waist. Thus, a belted diaper can be fitted to standing wearers and can be easily inspected for soiling without completely removing the diaper. Further, adult wearers often find the belted absorbent article designs easier to put on without assistance. However, belted diapers are generally more costly than conventional diapers and some wearers prefer the conventional design to the belted design.

Another popular diaper design has been the "pull-up" type, used in training pants and incontinence briefs. The "pull-up" design allows the wearer to pull the absorbent article on as pants and does not require any of the fastening steps of the conventional or belted type absorbent article designs. Although this feature is desirable for many adult users and children in their toilet training stage, the "pull-up" design is impractical for many users. Current "pull-up" designs lack any features that allow the diaper to be checked for soiling without removal of the diaper and the wearer's outer clothing.

Thus, it would be advantageous to provide an absorbent article having a fastening system that allows the user to construct and fasten the absorbent article in different configurations.

Therefore, it is an objective of the present invention to provide an absorbent article having a refastenable fastening system designed to allow the absorbent article to be constructed in a conventional, belted or "pull-up" configuration.

These and other objectives of the present invention will be more readily apparent when considered in reference to the following description and when taken in conjunction with the accompanying drawings.

SUMMARY OF THE INVENTION

The present invention provides absorbent articles such as disposable diapers, incontinent briefs, diaper holders, training pants and the like, having a fastening system that provides the user with different options as to how the absorbent article will be constructed and fitted to the wearer. The fastening systems allow the wearer to choose between conventional, belted, and pull-up diaper configurations. Further, the fastening systems are designed to ensure easy changing and removal of the absorbent article as well as easy inspection for soiling. Such absorbent articles comprise a containment assembly generally comprising a liquid pervious topsheet, a liquid impervious backsheet, an absorbent core disposed between the topsheet and the backsheet; first and second belt flaps extending outwardly from opposite sides of the containment assembly; and a refastenable fastening systems comprising a first fastening assembly for fastening the diaper in a belted configuration, and a second fastening assembly for fastening the diaper in a conventional configuration.

The first fastening assembly is designed for constructing the absorbent article in a belted configuration. Accordingly, the first fastening assembly comprises fastening elements disposed on the first belt flap and the second belt flap of the absorbent article, the outer surface of the belt, and the inner surface of the containment assembly in the front section. In use, the belted configuration is constructed by engaging the fastening element disposed on the first belt flap with the fastening element disposed on the second belt flap to form a belt. The fastening elements disposed on the front section of the containment assembly are then engaged with the fastening elements disposed on the outer surface of the belt to complete the construction in the belted configuration.

The second fastening assembly, designed as an alternative to the first fastening assembly, provides a system for fastening the absorbent article in a conventional configuration. Accordingly, the second fastening assembly comprises fastening members disposed on the inner surface of the first belt flap and the second belt flap and a fastening element disposed on the outer surface of the containment assembly in the front section. The absorbent article is constructed in the conventional configuration by engaging the fastening elements disposed on the first belt flap and the second belt flap with the fastening element disposed on the outer surface of the containment assembly in the front section.

In a preferred embodiment of the present invention, the diaper constructed in either the belted or the conventional configuration can be pulled on and off as a training pant. This option is provided by the special stretch characteristics of the waist and belt features. The waist and belt features are capable of maintaining sufficient tension to hold the diaper on the wearer throughout the period of use while providing enough stretch to allow the diaper to pulled down over the wearer's hips without detaching the fasteners. Thus, in a preferred embodiment of the present invention, the design of the diaper and the fastening system provides a diaper that can be fitted to the wearer in a conventional configuration or a belted configuration, either of which may be pulled on and off as a training pant if desired.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, and the like.

Figure 1:
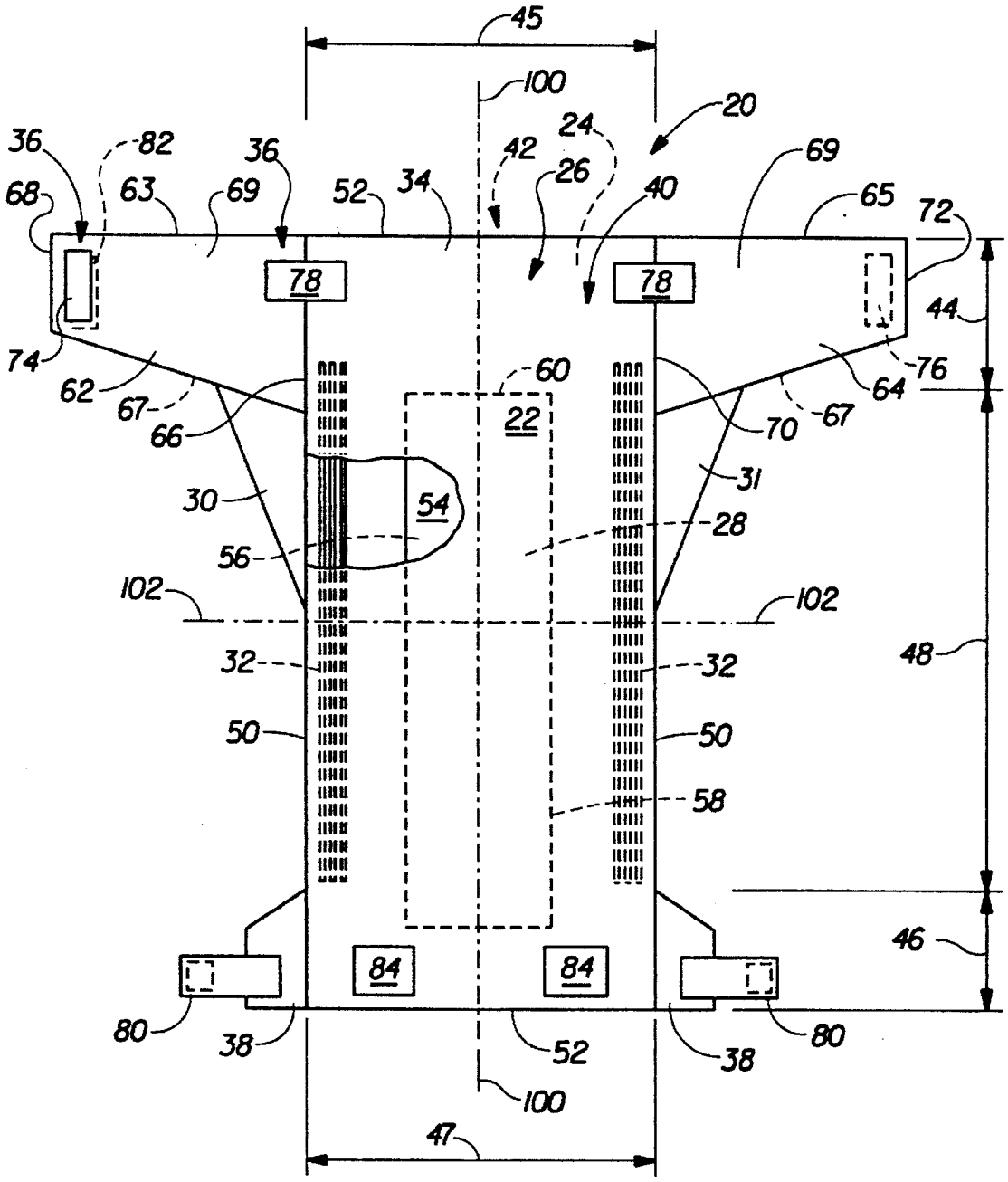
FIG. 1 is a plan view of a disposable diaper embodiment of the present invention having portions cut away to reveal underlying structure, the outer surface of the diaper is facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces away from the wearer, the outer surface 40, facing the viewer. As shown in FIG. 1, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The diaper preferably further comprises elasticized leg cuffs 32; ear flaps 38; an elastic waist feature 34; a first belt flap 62; a second belt flap 64; a first thigh panel 30; a second thigh panel 31; and a fastening system 36 comprising a first fastening assembly for constructing the diaper 20 in a belted configuration, and a second fastening assembly for fastening the diaper 20 in a conventional configuration.

The diaper 20 is shown in FIG. 1 to have an outer surface 40 (facing the viewer in FIG. 1), an inner surface 42 opposed to the outer surface 40, a rear waist region 44, a front waist region 46 opposed to the rear waist region 44, a crotch region 48 positioned between the rear waist region 44 and the front waist region 46, and a periphery which is defined by the outer perimeter or edges of the diaper 20 in which the longitudinal edges are designated 50 and the end edges are designated 52. The inner surface 42 of the diaper 20 comprises that portion of the diaper 20 which is positioned adjacent to the wearer's body during use (i.e., the inner surface 42 generally is formed by at least a portion of the topsheet 24 and other components joined to the topsheet 24). The outer surface 40 comprises that portion of the diaper 20 which is positioned away from the wearer's body (i.e., the outer surface 40 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 44 and the front waist region 46 extend from the end edges 52 of the periphery to the crotch region 48. The rear waist region 44 comprises a central region 45 and two belt flaps, the first belt flap 62, and the second belt flap 64, which typically comprise the outer lateral portions of the rear waist region 44. The front waist region 46 comprises a central region 47 and a pair of ear flaps designated 38, which typically comprise the outer lateral portions of the front waist region 46.

The diaper 20 also has two centerlines, a longitudinal centerline 100 and a transverse centerline 102. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

Figure 2:
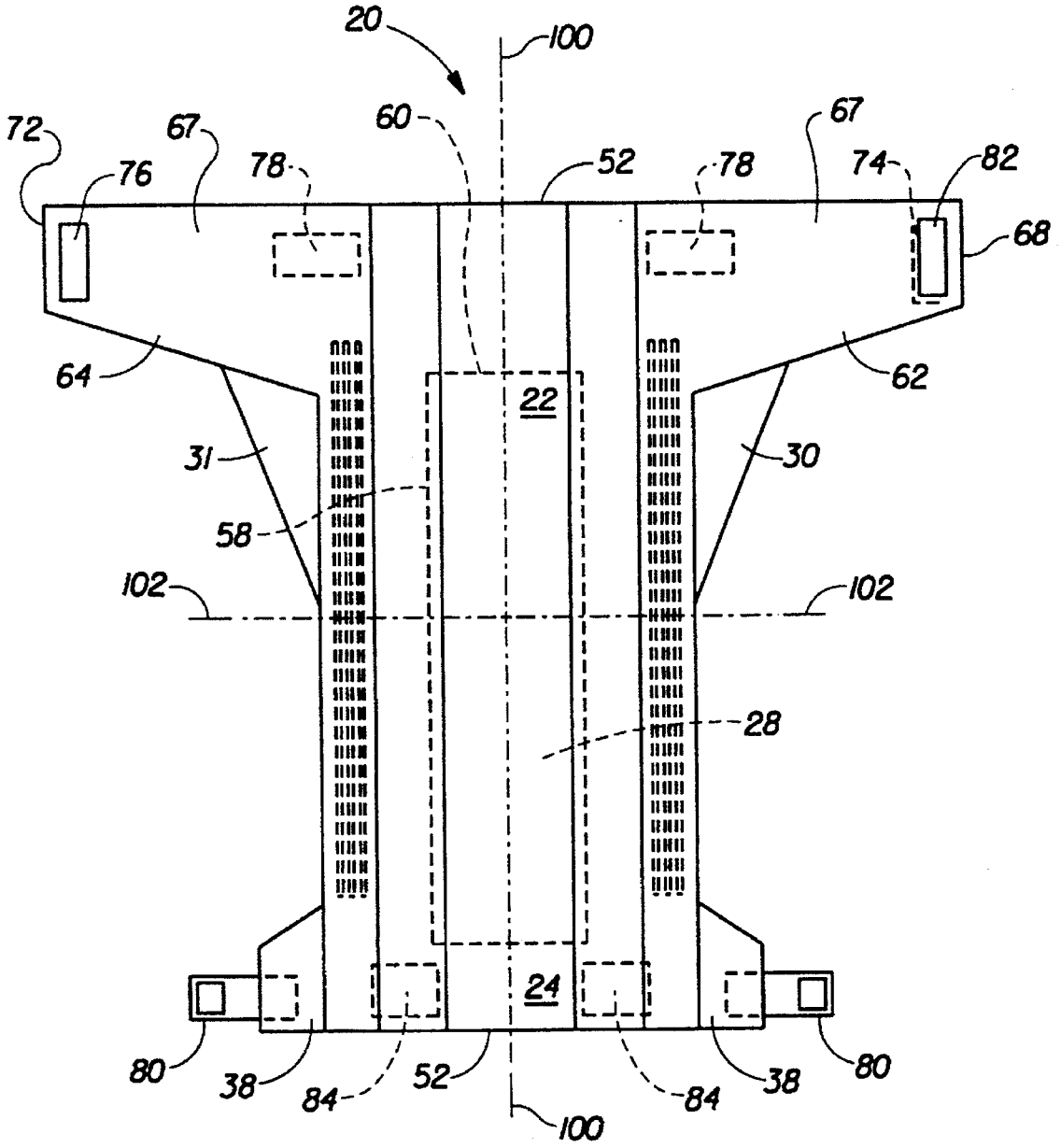
FIG. 2 is a plan view of a disposable diaper embodiment of the present invention, the inner surface of the diaper is facing the viewer.
Figure 3:
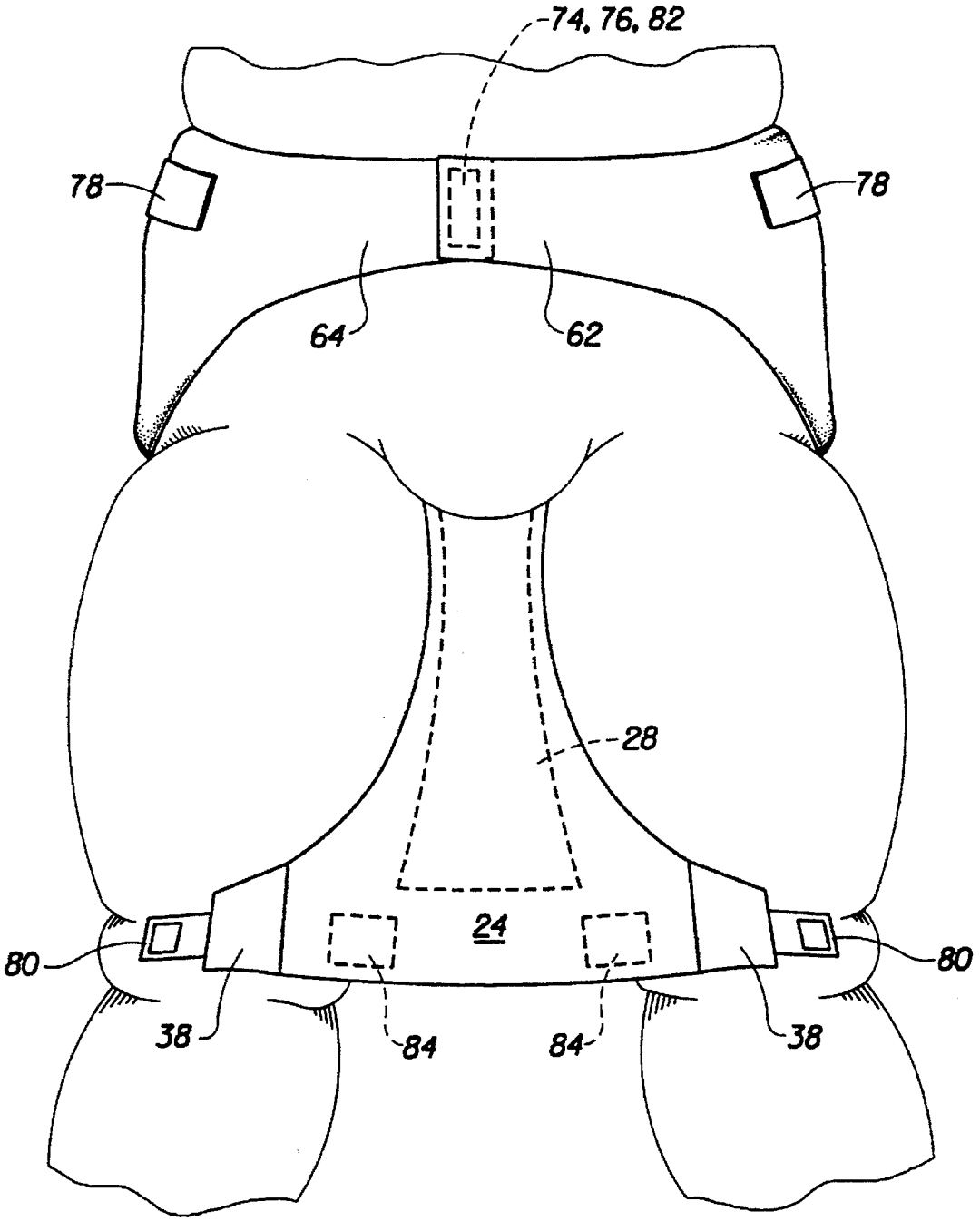
FIG. 3 is a front elevational view of the diaper being fitted onto the wearer in the belted configuration.
Figure 4:
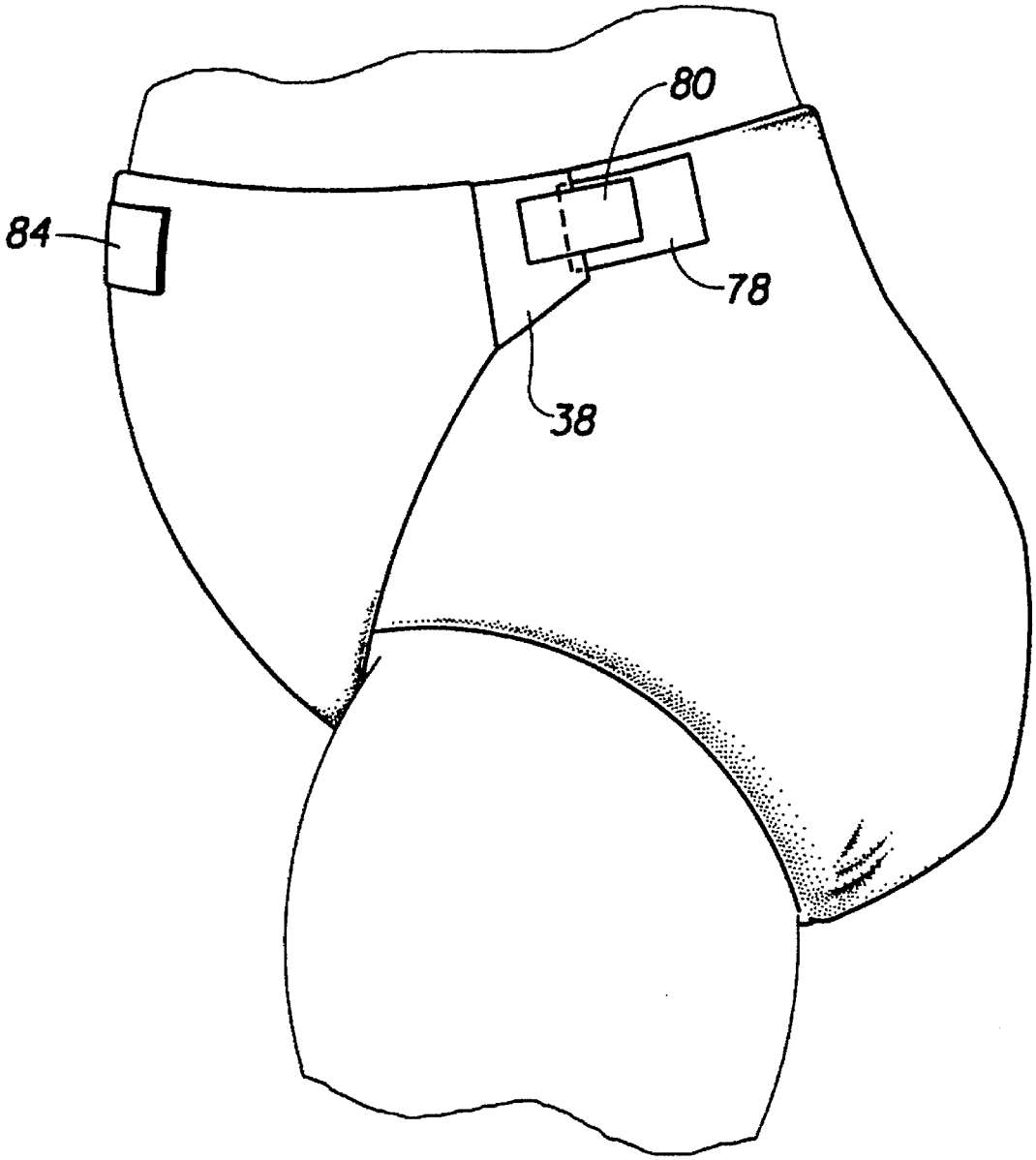
FIG. 4. is a side elevational view of the diaper fitted onto the wearer in the belted configuration.

FIG. 2 shows a preferred embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; each of which is incorporated herein by reference.

The absorbent core 28 may be any absorbent member which is generally compressible, conformable, non-irritating to the wearer's skin, and capable of absorbing and retaining liquids such as urine and other certain body exudates. As shown in FIG. 1, the absorbent core 28 has a garment-facing side 54, a body-facing side 56, a pair of side edges designated 58, and a pair of waist edges designated 60. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20.

One embodiment of the diaper 20 has an asymmetric, modified T-shaped absorbent core 28 having ears in the first waist region but a generally rectangular shape in the second waist region. Exemplary absorbent structures for use as the absorbent core 28 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The backsheet 26 is positioned adjacent the garment-facing surface 54 of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as ITL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art. Embodiments of the present invention are also contemplated wherein the absorbent core is not joined to the backsheet 26, the topsheet 24, or both in order to provide greater extensibility in the front waist region 46 and the rear waist region 44.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments, however, the backsheet 26 may permit vapors to escape from the absorbent core 28 (i.e., is breathable). Thus, the backsheet 26 preferably comprises a woven or nonwoven material, polymeric films such as thermoplastic films of polyethylene or polypropylene, or composite materials such as a film-coated nonwoven material. A suitable backsheet 26 is a thermoplastic film having a thickness of from about 0.012 mm (0.5 mil) to about 0.051 mm (2.0 mils). Preferably, the backsheet 26 is embossed and/or matte finished to provide a more clothlike appearance.

In preferred embodiments of the present invention, at least a portion of the backsheet 26 is subjected to mechanical stretching in order to provide both a "zero strain" stretch laminate that forms the thigh panels 30 and 31 and to prestrain the portion of the backsheet 26 coinciding with the elastic waist feature 34. The backsheet 26 can be prestrained by directing the backsheet through an incremental mechanical stretching system similar to the operation described with respect to the formation of the "zero strain" stretch laminate backsheet and elasticized side panels in U.S. Pat. No. 5,151,092 entitled "Absorbent Article With Dynamic Elastic Waist Feature Having A Predisposed Resilient Flexural Hinge", issued to Buell et al., on Sep. 29, 1992. Accordingly, the backsheet is preferably elongatable, more preferably drawable, but not necessarily elastomeric, so that the backsheet 26 will, upon mechanical stretching, be at least to a degree permanently elongated such that it will not fully return to its original undistorted configuration. In preferred embodiments, the backsheet 26 can be subjected to mechanical stretching without undue rupturing or tearing. Thus, it is preferred that the backsheet 26 have an ultimate elongation to break of at least 400% to about 700% in the cross-machine direction as measured using a method consistent with ASTM (American Society of Testing Materials) D-638. Films suitable for use as the backsheet 26 generally contain a high content of linear low density polyethylene. The Clopay Corporation of Cincinnati, Ohio, manufactures a suitable backsheet under the designation 1401. Other suitable materials for the backsheet 26 include RR8220 blown films and RR5475 cast films as manufactured by Tredegar Industries, Inc. of Terre Haute, Ind.

Alternatively, the backsheet 26 or portions of the backsheet 26 may comprise a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-path length which is greater than that of the other region as measured substantially parallel to the predetermined axis while the material is in an untensioned condition. The region exhibiting the longer surface-path length includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-path length to enter the plane of applied elongation, whereupon the SELF web exhibits second resistive forces to further elongation. The total resistive forces to elongation are higher than the first resistive forces to elongation provided by the first region.

The strainable web material can, in a preferred embodiment, comprise a formed polymeric film. The strainable web material can be made of a base material that has a relatively low extensibility under the forces the diaper is normally subjected to when worn. When formed into the strainable web material as described herein, however, the base material, thus formed, will be extensible under these forces. The strainable web material can also be formed into a structure that provides a "force wall" to be created at specific, pre-selected elongations and forces. The strainable web material is preferably comprised substantially of linear low density polyethylene (LLDPE). The strainable web material may also be comprised of other polyolefins such as polyethylenes, including low density polyethylene (LDPE), ultra low density polyethylene (ULDPE), high density polyethylene (HDPE), or polypropylene and blends thereof with the above and other materials. Examples of other suitable polymeric materials which may also be used include, but are not limited to polyester, polyurethanes, compostable or biodegradable polymers, heat shrink polymers, thermoplastic elastomers, and breathable polymeric structures.

The strainable web material can be used in various different forms in the diaper 20. One example of a suitable form of structural elastic-like film is a laminate. The laminate comprises a strainable web material secured between two longitudinally extensible, preferably carded nonwoven webs. (In addition, the strainable web material can also be used in the various other components of the absorbent article described herein.)

Figure 6:
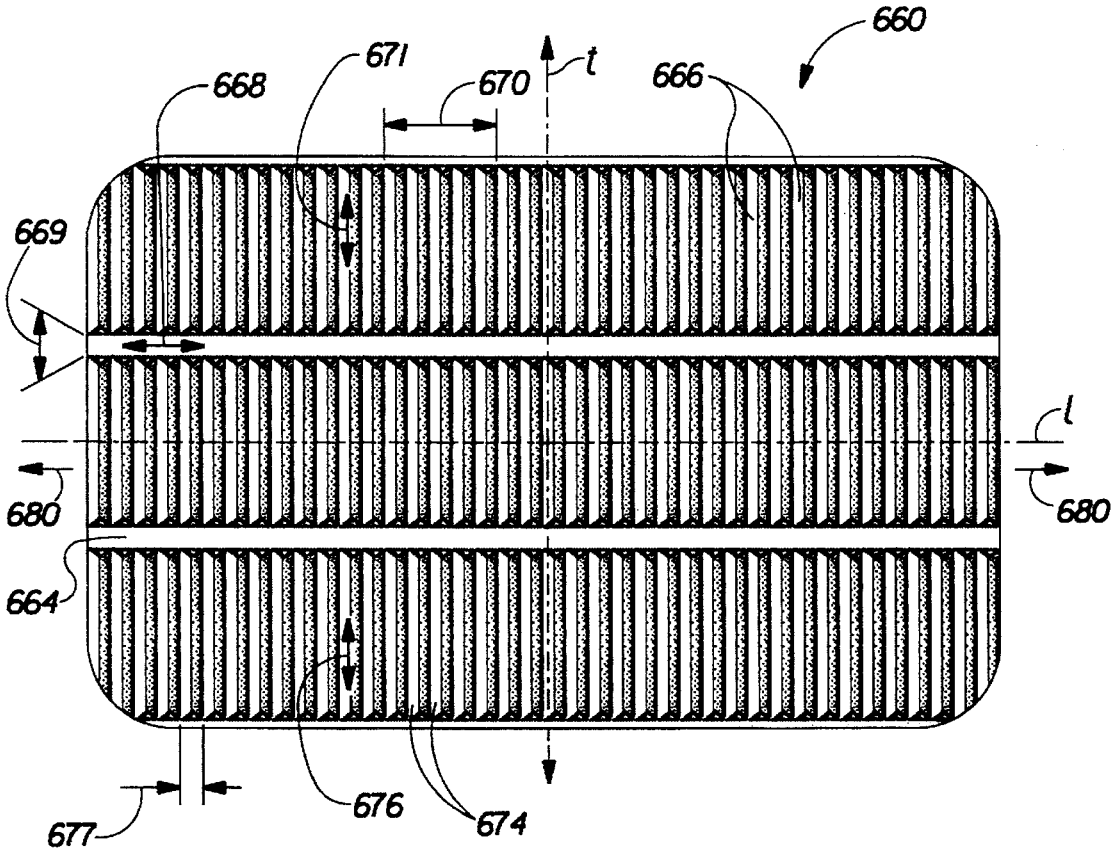
FIG. 6 is a plan view drawing of a preferred embodiment of a polymeric web material having a strainable network with the deformations facing the viewer.
Figure 7:
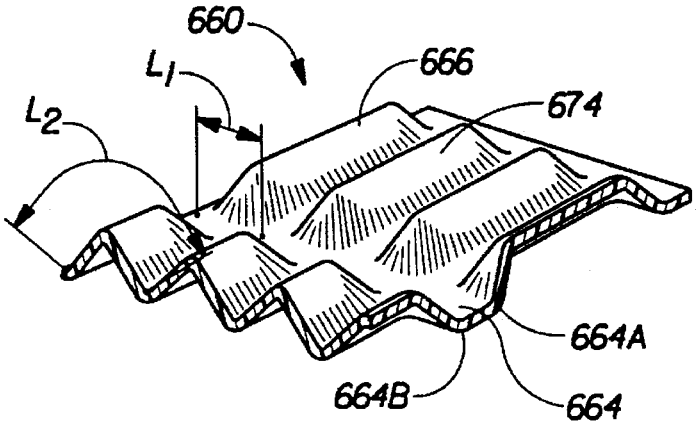
FIG. 7 is a segmented, perspective illustration of the polymeric web material of FIG. 6 in an untensioned condition.
Figure 8:
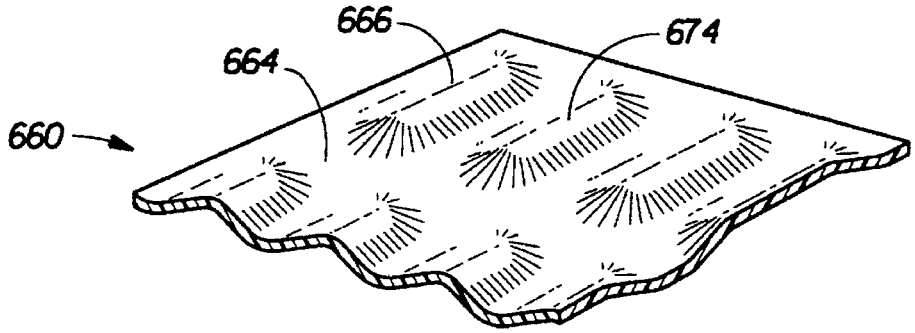
FIG. 8 is a segmented, perspective illustration of the polymeric web material of FIG. 6 in a tensioned condition corresponding to stage I on the force-elongation curve depicted in FIG. 10.

The strainable web material is shown in FIGS. 6 and 7 in its substantially untensioned condition. The strainable web material has two centerlines, a longitudinal centerline, which is also referred to hereinafter as an axis or direction "l" and a transverse or lateral centerline, which is also referred to hereinafter as an axis or direction "t". The lateral centerline "t" is generally perpendicular to the longitudinal centerline "l". In a preferred embodiment, the longitudinal centerline 1 of the strainable web material is aligned with the longitudinal centerline 100 of the diaper 20. In other embodiments, however, the longitudinal centerline 1 of the web material can be oriented in other directions, depending on the direction of extensibility desired.

As shown in FIGS. 6 and 7, strainable web material 660 includes a "strainable network" of distinct and dissimilar regions. As used herein, the term "strainable network" refers to an interconnected and interrelated group of regions which are able to be extended to some useful degree in a predetermined direction providing the strainable web material with an elastic-like, relatively low resistive force stage and a relatively high resistive force stage. The strainable network includes at least a first region 664 and a second region 666. The first region 664 has an elastic modulus E1 and a cross-sectional area A1. The second region 666 has a modulus E2 and a cross-sectional area A2. The first and second regions each have a first surface and an opposing second surface. In the preferred embodiment shown in FIGS. 6 and 7, the strainable network includes a plurality of first regions 664 and a plurality of second regions 666. The first regions 664 have a first axis 668 and a second axis 669, wherein the first axis 668 is preferably longer than the second axis 669. The first axis 668 of the first region 664 is substantially parallel to the longitudinal axis, l, of the strainable web material 660 while the second axis 669 is substantially parallel to the transverse axis, t, of the strainable web material 660. The second regions 666 have a first axis 670 and a second axis 671. The first axis 670 is substantially parallel to the longitudinal axis of the strainable web material, while the second axis 671 is substantially parallel to the transverse axis of the strainable web material. In the preferred embodiment of FIG. 6, the first regions 664 and the second regions 666 are substantially linear, extending continuously in a direction substantially parallel to the longitudinal axis of the strainable web material.

In the illustrated embodiment, a portion of the strainable web material has been "formed" such that the entire strainable web material exhibits a controlled resistive force along a predetermined axis (which in the case of the illustrated embodiment is substantially parallel to the longitudinal axis of the web material) when subjected to an applied axial elongation in a direction substantially parallel to the longitudinal axis. As used herein, the term "formed" refers to the creation of a desired structure or geometry upon the web material that will substantially retain the desired structure or geometry when it is not subjected to any externally applied elongations or forces. Suitable methods for forming a material such as the strainable web material described herein include, but are not limited to embossing by mating plates or rolls, thermoforming, high pressure hydraulic forming, or casting.

The web material used in the present invention is comprised of a strainable network of contiguous, "distinct", and "dissimilar" regions, wherein the strainable network includes at least a first region and a second region, where the first region has a "surface-path length" less than that of the second region. The surface path length is measured parallel to a predetermined axis when the material is in an untensioned state. As used herein, the term "formed portion" refers to the portion of the material which is comprised of the desired structure or geometry of the strainable network. As used herein, the term "surface-path length" refers to a measurement along the topographic surface of the region in question in a direction parallel to the predetermined axis. As used herein, the term "distinct" or "dissimilar" when referring to regions, refers to regions within the strainable network having measurably different surface-path lengths as measured parallel to a predetermined axis while the web material is in an untensioned condition.

In a preferred embodiment shown in FIGS. 6 and 7, the first regions 664 comprise a substantially planar region. That is, the material within the first region 664 is in substantially the same condition before and after the formation step undergone by strainable web material. The second regions 666 include a plurality of continuous, interconnected, deformations 674 which extend alternately beyond the plane of both the first and second surfaces (664A and 664B, respectively) of first region 664. In other embodiments, the deformations 674 may extend beyond the plane of only one of either the first or the second surfaces of the first region.

The deformations 674 have a first axis 676 which is substantially parallel to the transverse axis of the web material and a second axis 677 which is substantially parallel to the longitudinal axis of the strainable web material. The first axis 676 of the deformations 74 is at least equal to, and preferably longer than the second axis 677. To enhance the two-stage resistive force versus elongation behavior characteristics of (the side flap) of the present invention, the ratio of the first axis 676 to the second axis 677 is at least 1:1, and preferably at least 2:1 or greater. In general, the greater this ratio, the more pronounced will be the two-stage resistive force versus elongation characteristic of the web material.

The first region 664 and the second region 666 each have a "projected path length". As used herein the term "projected path length" refers to length of a region as viewed perpendicularly to the surface of the web material measured parallel to the pre-determined axis (i.e., parallel to the longitudinal axis) of the strainable web material 660. The projected path length of the first region 664 and the projected path length of the second region 666 are equal to one another.

However, as shown in FIG. 7, the first region 664 has a surface-path length, L1, less than the surface-path length, L2, of the second region 666 as measured topographically parallel to the longitudinal axis of the web material while the web material is in an untensioned condition. To enhance the two-stage resistive force versus elongation behavior characteristic of the strainable web material 660, the surface-path length of the second region 666 is at least about 15 percent greater than that of the first region, more preferably about 30 percent greater than that of the first region, and most preferably at least about 70 percent greater than that of the first region.

The web material 660 exhibits a modified "Poisson lateral contraction effect" substantially less than that of an otherwise identical unformed web material of the prior art. As used herein, the term "Poisson lateral contraction effect" describes the lateral contraction behavior of a material which is being subjected to an applied elongation. Preferably the Poisson lateral contraction effect of the web material of the present invention is less than about 0.4 when the web is subjected to about 20 percent elongation. Preferably, the web material exhibits a Poisson lateral contraction effect less than about 0.4 when the web material is subjected to about 40, 50, or even 60 percent elongation. More preferably, the Poisson lateral contraction effect is less than about 0.3 when the web material is subjected to 20, 40, 50, or 60 percent elongation.

For the strainable web material, the direction of applied axial elongation, indicated by arrows 680, is substantially perpendicular to the first axis 676 of the deformations 674. (The amount of axial elongation is distance, D.) As the deformations 674 are able to extend in a direction substantially perpendicular to their first axis 676, the direction of applied axial elongation to cause extension in strainable web material is also substantially perpendicular to the first axis 676 of the deformations 674.

While the direction of applied axial elongation, indicated by arrows 680, is substantially perpendicular to the first axis 676 of the deformations 674, an applied axial elongation having a longitudinal component will cause the strainable web material to extend in the direction of applied axial elongation.

Figure 10:
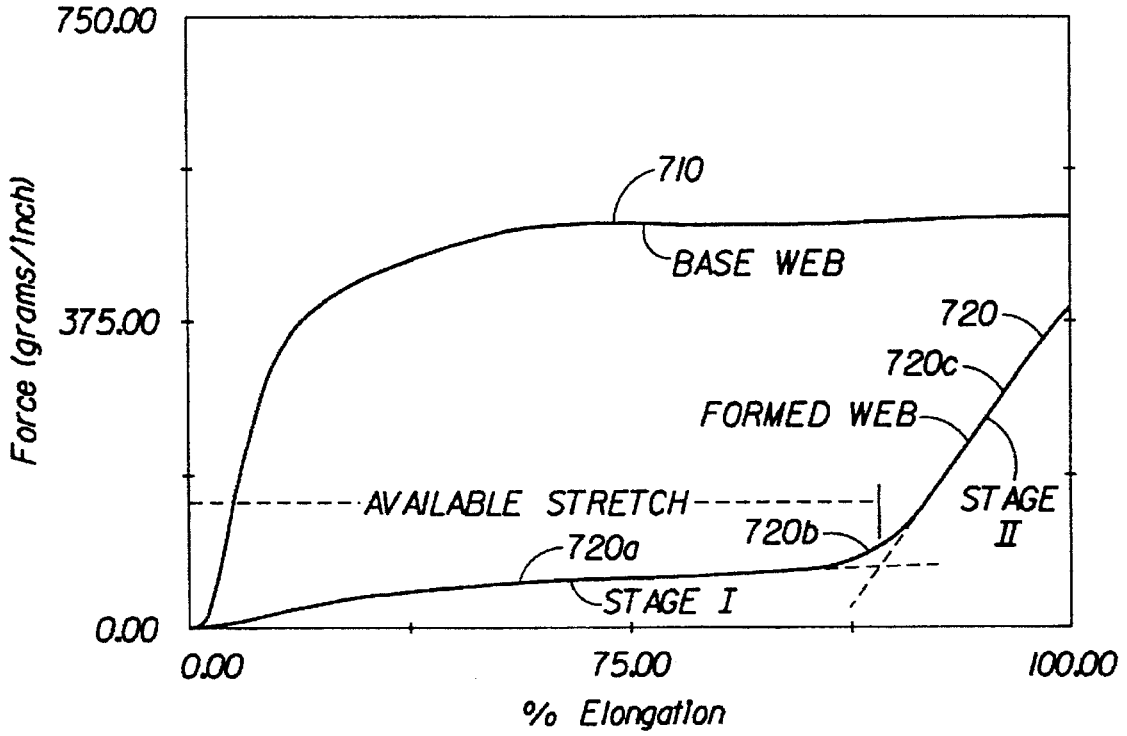
FIG. 10 is a graph of the resistive force verses percent elongation comparing the behavior of the polymeric web material of FIG. 6, with an otherwise identical, planar base polymeric web material.

In FIG. 10 there is shown an exemplary graph of a resistive force-elongation curve 720 of a formed polymeric web material of the present invention along with a similar curve 710 for a planar, base polymeric film from which the web material is formed. Referring now to the force-elongation curve 720, there is an initial substantially linear, lower force versus elongation stage I designated 720*a*, a transition zone designated 720*b*, and a substantially linear stage II designated 720*c* which displays substantially higher force versus elongation behavior, corresponding to a resistive force wall beyond which the web material may undergo additional permanent deformation.

Figure 9:
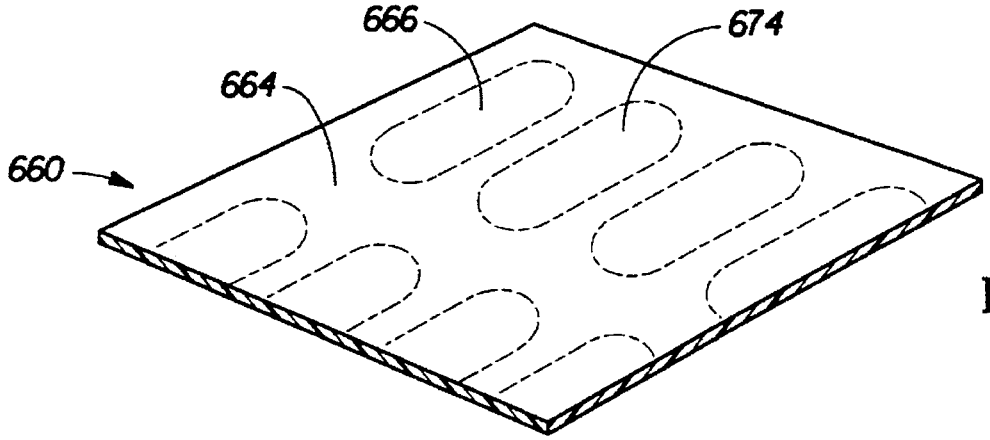
FIG. 9 is a segmented, perspective illustration of the polymeric web material of FIG. 6 in a tensioned condition corresponding to stage II on the force-elongation curve depicted in FIG. 10.

As seen in FIG. 10 a formed web material having a strainable network exhibits a controlled multi-stage behavior when subjected to an applied elongation in a direction parallel to the longitudinal axis of the web material. The resistive force to the applied elongation is significantly different between stage I (720*a*) and stage II (720*c*) of curve 720 as compared to curve 710 which does not exhibit this behavior. Referring now to FIG. 7, as the web material is subjected to an applied axial elongation indicated by arrows 680 in FIG. 6, the first region 664 having the shorter surface-path length, L1, provides most of the initial resistive force, P1, to the applied elongation which corresponds to stage I. While in stage I, the deformations 674 in the second region 666 are mostly out of the plane of applied elongation and offer minimal resistance to the applied elongation. In the transition zone between stages I and II, the deformations 674 are becoming aligned with the applied elongation. In stage II, as seen in FIG. 9, the deformations 674 in the second region 666 have become substantially aligned with the plane of applied elongation and begin to resist further elongation. The second region 666 now contributes a second resistive force, P2, to further elongation. The first and second resistive forces to elongation provide a total resistive force, PT, which is greater than the resistive force provided by the first region 664. Accordingly, the general slope of the force-elongation curve in stage II displays the characteristics of a force wall that is significantly greater than the general slope of the force-elongation curve in stage I.

The resistive force P1 is substantially greater than the resistive force P2 when (L1+D) is less than L2. While (L1+D) is less than L2 the first region 664 provides an initial resistive force, P1, generally satisfying the equation:

$$P1 = \frac{(A1*E1*D)}{L1}$$

When (L1+D) is greater than L2 the first and second regions provide a combined total resistive force, PT, to the applied elongation D, generally satisfying the equation:

$$PT = \frac{(A1*E1*D)}{L1} + \frac{(A2*E2*|L1+D-L2|)}{L2}$$

(Where "*" represents a multiplication sign.)

The maximum elongation occurring while in stage I is considered to be the "available stretch" of the web material. The available stretch can be effectively determined by inspection of the force-elongation curve 720, the approximate point at which there is an inflection in the transition zone between stage I and stage II is the percent elongation point of "available stretch". The range of available stretch can be varied from about 10% to 100% or more; this range of elastic-like response is often found to be of interest in disposable absorbent articles, and can be largely controlled by the extent to which surface-path length L2 in the second region 666 exceeds surface-path length L1 in the first region 64 and the properties of the base film. Significantly higher forces are required to achieve percent elongations in the base film equivalent to those percent elongations in the web 660. The approximate extent of stage I can be controlled as desired by adjusting the path lengths, L1 and L2 in an untensioned condition. The force-elongation behavior of stage I can be controlled by adjusting the width, thickness, and spacing of first region 664 and the properties of the base film.

When the web material of FIG. 6 is subjected to an applied elongation, the web material exhibits an elastic-like behavior as it extends in the direction of applied elongation and retracts to its substantially untensioned condition once the applied force is removed, unless extended to the point of yielding. The web material is able to undergo multiple applications of applied elongation without losing its ability to substantially recover. Accordingly, the web material is able to retract to its substantially untensioned condition once the applied elongation or force is removed.

While the web material may be easily and reversibly extended in the direction of applied axial elongation, in a direction substantially perpendicular to the first axis 676 of the deformations 674, web material is relatively non-extensible in a direction substantially parallel to the first axis 676 of the deformations 674. The plastic deformation imparted upon the deformations 674 allows the deformations to be extended in one direction, in a direction substantially perpendicular to the first axis of the deformations, while being relatively non-extensible in a direction substantially perpendicular to the direction of extension, in a direction substantially parallel to the first axis of the deformations. In other embodiments, the strainable web material 660 can be provided with first regions 664 that extend outward from a center and second regions 666 that are disposed in concentric circles around the center to make the strainable web material 660 extensible in more than one direction.

The amount of applied force required to extend the web material is dependent upon the inherent properties of the base material forming the web material and the width and spacing of the undeformed regions 664, with narrower and more widely spaced undeformed regions 664 requiring lower extensional forces to achieve the desired elongation. The first axis 668, (i.e., the length) of the undeformed regions 664 is preferably greater than the second axis 669, (i.e., the width) with a preferred length to width ratio of between 5:1 and 300:1.

The depth and number of deformations 674 can also be varied to control the applied force or elongation required to extend the web material of the present invention. In one preferred embodiment, the deformations are formed by two rigid plates having outer dimensions of 5.0" by 12" by 0.75". On one surface of each plate are a series of meshing teeth which are substantially triangular in cross section and measure 0.030" at their bases and taper to a vertex with a radius of 0.008" at the top. The centerlines of the teeth are spaced evenly and at 0.030" increments. On the "toothed" side of one plate, a series of grooves are cut which are parallel to each other and perpendicular to the evenly spaced teeth. These grooves measure 0.031" wide and are continuous over the entire length of the plate, and are spaced at a distance of 0.25" on center. These grooves correspond to the undeformed regions of the deformed web of material.

The preferred LLDPE base material is placed between the plates in a hydraulic press having platens larger than the plates to evenly distribute pressure. The plates are compressed under a load of at least 4,000 pounds. The formed web material is then removed from between the plates. The available stretch or elongation is increased if for a given number of deformations, the height or degree of deformation imparted on the deformations is increased. Similarly, the available stretch or elongation is increased if for a given height or degree of deformation, the number or frequency of deformations is increased.

The size of the backsheet 26 is dictated by the size of the absorbent core 28 and the exact diaper design selected. In a preferred embodiment, the backsheet 26 has a modified hourglass shape extending beyond the absorbent core a minimum distance of a bout 1.3 cm to about 2.5 cm (about 0.5 to about 1.0 inch) around the entire diaper periphery. Preferably, the backsheet 26 is much wider than the absorbent core in the rear waist region 44 so that the side panels 30 in the rear waist region 44 are generally wider in the lateral direction than the ear flaps 38 in the front waist region 46.

The topsheet 24 is positioned adjacent the body-facing surface 56 of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the diaper periphery and are indirectly joined together by directly joining them to the absorbent core 28 by the attachment means (not shown).

The topsheet 24 is compliant, soft feeling, and non-irritating to the wearer's skin. Further, the topsheet 24 is preferably liquid pervious permitting liquids (e.g., urine) to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is preferably made of a hydrophobic material to isolate the wearer's skin from liquids which have passed through the topsheet 24 and are contained in the absorbent core 28 (i.e. to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

In a preferred embodiment of the present invention, at least a portion of the topsheet 24 is subjected to mechanical stretching in order to provide a "zero strain" stretch laminate that forms the thigh panels 30 and 31. The topsheet 24 can be prestrained by any methods as are known in the art including, but not limited to, the methods described herein with respect to the formation of the "zero strain" stretch backsheet. Thus, the topsheet 24 is preferably elongatable, more preferably drawable, but not necessarily elastomeric, so that the topsheet 24 will, upon mechanical stretching, be at least to a degree permanently elongated such that it will not fully return to its original configuration. In preferred embodiments, the topsheet 24 can be subjected to mechanical stretching without undue rupture or tearing. Thus, it is preferred that the topsheet 24 have a low cross-machine direction (lateral direction) yield strength.

There are a number of manufacturing techniques which may be used to manufacture the topsheet 24. For example, the topsheet 24 may be a nonwoven web of fibers. When the topsheet 24 comprises a nonwoven web, the web may be spunbonded, carded, wetlaid, melt-blown, hydroentangled, combinations of the above, or the like. A suitable topsheet 24 is carded and thermally bonded by means well known to those skilled in the fabrics art. A satisfactory topsheet 24 comprises staple length polypropylene fibers having a denier of about 2.2 As used herein, the term "staple length fibers" refers to those fibers having a length of at least about 15.9 mm (0.625 inches). Preferably, the topsheet 24 has a basis weight from about 14 to about 25 grams per square meter. A suitable topsheet is manufactured by Veratec, Inc., a Division of International Paper Company, of Walpole, Mass. under the designation P-8.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff(gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment. Each of these patents are incorporated herein by reference. While each elasticized leg cuff 32 may be configured so as to be similar to any of the leg bands, side flaps, barrier cuffs, or elastic cuffs described above, each elasticized leg cuff 32 preferably comprises a gasketing cuff as described in the above-referenced U.S. Pat. No. 3,860,003 and a barrier cuff as described in the above-referenced U.S. Pat. No. 4,909,803.

In a preferred embodiment of the present invention, the diaper 20 also comprises ear flaps 38 that extend laterally outwardly from each longitudinal edge 50 of the containment assembly 22 in the front waist region 46. The ear flaps 38 provide a structure to which the rear waist region 44 can be attached when the diaper 20 is constructed in a conventional diaper configuration. Alternatively, the ear flaps 38 can provide a structure that is attached to the rear waist region 44 of the diaper 20 when the diaper 20 is constructed in a belted configuration. The ear flaps 38 may take on a number of different sizes, shapes, configurations, and materials. The ear flaps 38 may comprise a portion of the material making up one or more of the diaper elements, including the topsheet 24, and the backsheet 26. Alternatively, the ear flaps 38 may comprise a separate element or a plurality of elements affixed to the diaper. Suitable materials for use as the ear flaps 38 include woven webs; nonwoven webs; films, including polymeric films; foams; laminate materials including film laminates, nonwoven laminates, or zero strain laminates; formed films; elastomers; composites; structural elastic like-film (SELF) webs or any combination of materials hereinafter described or as described with respect to the extensible thigh panels 30 and 31 as are known in the art. The ear flaps 38 may be joined to the containment assembly 22 by any means as known in the art; for example the ear flaps 38 may be continuously or intermittently bonded to the containment assembly 22 using adhesive, heat bonding, pressure bonding, ultrasonic bonding, dynamic mechanical bonding or any other method that is known in the art.

The diaper 20 preferably further comprises an elastic waist feature 34 that helps provide improved fit and containment. The elastic waist feature 34 is that portion or zone of the diaper 20 which is intended to elastically expand and contract to dynamically fit the wearer's waist. The elastic waist feature 34 preferably extends longitudinally outwardly from at least one of the waist edges 60 of the absorbent core 28 and generally forms at least a portion of the end edge 52 of the diaper 20. Disposable diapers are generally constructed so as to have two elastic waist features, one positioned in the rear waist region 44 and one positioned in the front waist region 46, although diapers can be constructed with a single elastic waist feature. Further, while the elastic waist feature 34 or any of its constituent elements can comprise a separate element affixed to the diaper 20, the elastic waist feature 34 may be constructed as an extension of other elements of the diaper such as the backsheet 26 or the topsheet 24, preferably both the backsheet 26 and the topsheet 24.

The elastic waist feature 34 may comprise any suitable stretchable or elastomeric materials. (As used herein, the term "stretchable" refers to materials that are extensible when forces are applied to the material, and offer some resistance to extension. The term "elastomeric" refers to materials that extend in at least one direction when a force is applied to the material, and return to approximately their original dimensions after the force is released.) Suitable elastomeric materials for use as the elastic waist feature 34 are described hereinbelow with respect to the extensible side panels 30.

The elastic waist feature 34 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell; each of these references being incorporated herein by reference. Further, the elastic waist feature 34 may comprise "pleats" that may be activated by the diaperer to provide additional extension in the waist regions. (As used herein, the term "pleats" refers to regions of material that have been folded back upon themselves such that when an activation force is applied the material unfolds.) This additional extension provided by this pleated configuration is desirable when the diaper 20 is fitted to the wearer in either the conventional or the belted configuration and removed by pulling the diaper off the wearer without detaching the fastening system.

In a particularly preferred embodiment of the present invention, the diaper 20 additionally comprises two thigh panels, such as a first thigh panel 30 and a second thigh panel 31, as shown in FIG. 1. When the diaper 20 is fitted to the wearer, the thigh panels 30 and 31 cover the buttocks of the wearer and encircle the outer portion of the wearer's legs. The thigh panels 30 and 31 extend laterally outwardly from, and are disposed along the longitudinal edges 50 of the containment assembly 22 in the crotch region 48. (The term "disposed" as used herein means that an element(s) of the diaper is formed (joined and positioned) in a particular place or position as a unitary structure with other elements of the diaper or a separate element joined to another element of the diaper.) As shown in FIG. 1, the first thigh panel 30 is joined to the first belt flap 62 and extends generally longitudinally from the first belt flap 62 along one of the longitudinal edges 50 of the containment assembly 22 to a location in the crotch region 48. Likewise, the second thigh panel 31 is joined to the second belt flap 64 and extends generally longitudinally from the second belt flap 64 to a location adjacent the other longitudinal edge 50 of the containment assembly 22 in the crotch region 48.

The thigh panels 30 and 31 may take on a number of different sizes, shapes, materials and configurations. In a preferred embodiment, the thigh panels are extensions of the topsheet 24, the backsheet 26, or both. However, the thigh panels may comprise separate elements that are joined to the diaper 20. Examples of materials suitable for use in the thigh panels are hereinbefore described with respect to the topsheet 24 and the backsheet 26. In an especially preferred embodiment, at least a portion of the material forming the thigh panels is subjected to mechanical stretching in order to provide a "zero strain" stretch laminate extensible in at least the lateral direction. This allows the thigh panels to expand in conjunction with the motions of the wearer and reduces the possibility of red marks in the regions where the thigh panels contact the wearer. Examples of suitable methods for prestraining the material forming the thigh panels are described herein with respect to the topsheet and the backsheet and the above referenced U.S. Pat. No. 5,151,092 issued to Buell, et al. which is incorporated herein by reference. The thigh panels 30 and 31 may be joined to the diaper 20 by any means as known in the art; for example the thigh panels may be continuously or intermittently bonded to the containment assembly 22 using adhesive, heat bonding, pressure bonding, ultrasonic bonding, dynamic mechanical bonding or any other method that is known in the art.

The diaper 20 additionally comprises a pair of belt flaps such as a first belt flap 62 and a second belt flap 64, as shown in FIG. 1. The belt flaps 62 and 64 encircle part of the waist of the wearer when the diaper 20 is fitted to the wearer. When the diaper is fitted to the wearer in the conventional configuration, the belt flaps 62 and 64 extend from the rear waist region 44 of the diaper 20 around the wearer's hips to the front waist region 46 of the diaper where the belt flaps 62 and 64 are fastened to the front waist region 46 forming the diaper's waist closure. In the belted configuration, the belt flaps 62 and 64 extend from the rear waist region 44 of the diaper 20 around the wearer's hips where the belt flaps 62 and 64 are fastened together to form a belt.

Each belt flap is preferably disposed adjacent one of the longitudinal edges 50 of the containment assembly 22, preferably in the rear waist region 44. While it is not necessary that the pair of belt flaps be identical, as shown in FIG. 1, they are preferably mirror images of one another. Each of the belt flaps 62 and 64 have a proximal edge, a distal edge, an end edge, an inner surface, and an outer surface. For example, the first belt flap 62 has a proximal edge 66 disposed adjacent one of the longitudinal edges 50 of the containment assembly 22 in the rear waist region 44 of the diaper 20, a distal edge 68 spaced laterally outwardly from the proximal edge 66, and an end edge 63 running between the proximal edge 66 and the distal edge 68. The second belt flap 64 has a proximal edge 70, a distal edge 72 and an end edge 65. As shown in FIG. 1, the end edges 63 and 65 of the belt flaps 62 and 64 can form a portion of the end edge 52 of the diaper 20, however, embodiments are contemplated wherein the end edges 63 and 65 do not form a portion of the end edge 52 of the diaper 20. The inner surface of each belt flap is designated 67 and the outer surface of each belt flap is designated 69. As shown in FIG. 1, the outer surface 69 of each belt flap is that surface which faces away from the wearer when the diaper is being worn and generally corresponds to the outer surface 40 of the containment assembly 22. As shown in FIG. 2, the inner surface 67 of each belt flap is that surface which faces the wearer when the diaper 20 is being worn and generally corresponds to the inner surface 42 of the containment assembly.

In a preferred embodiment of the present invention, the belt flaps 62 and 64 are at least partially elastically extensible in the lateral direction to provide a more comfortable and contouring fit. (As used herein, the term "elastically extensible" refers to materials that extend in at least one direction when a force is applied and return to approximately their original dimensions after the force is removed. The "lateral direction" is defined as the direction parallel to the transverse centerline 102 of the diaper.) Elastically extensible belt flaps also provide more effective application of the diaper since even if the diaperer fits the diaper to the wearer asymmetrically, the diaper will self adjust during wear to attain an improved fit. Further, elastically extensible belt flaps provide improved dynamic fit about the waist of the wearer, reducing the possibility of sagging or gapping, and sustaining the fit of the diaper throughout the time of wear.

The belt flaps 62 and 64 may take on a number of different sizes, shapes, configurations and materials. The exact length, width and thickness of the belt flaps 62 and 64 will vary depending on the dimensions of the intended user. It is important, however, that the belt flaps 62 and 64 be long enough in the lateral direction to completely encircle the waist of the wearer to ensure that the diaper can be properly fitted to the wearer in the belted configuration. (In embodiments comprising elastically extensible belt flaps, the dimensions of the belt flaps are preferably taken while the belt flaps are under some tension rather than when the belt flaps are in their relaxed condition. This ensures that the belt flaps will provide the diaper 20 with the advantages discussed above.) The belt flaps 62 and 64 may comprise a portion of the material making up one or more of the diaper elements, including the topsheet 24, the backsheet 26, or the waist feature 34. Alternatively, the belt flaps may comprise a separate element or a plurality of elements joined to the diaper 20. If the belt flaps 62 and 64 are separate elements joined to the diaper 20, they can be joined by any by any means as known in the art. Examples of suitable attachment means include adhesive bonding, heat bonding, pressure bonding, ultrasonic bonding, dynamic mechanical bonding or a combination of any of these means or any other means as are known in the art.

One elastically extensible material that has been found to be especially suitable for use in the belt flaps is a laminate of two coverstock layers with an elastomeric synthetic rubber foam sandwiched between the coverstock layers. (As used herein, the term "coverstock" refers to any woven or nonwoven materials.) An example of suitable coverstock material is hereinbefore discussed with respect to the topsheet 24 and the backsheet 26. Examples of suitable synthetic foams to be sandwiched between the coverstock layers include: a) crosslinked natural rubber foams preferably having a caliper of approximately 50 mils and a density of approximately 13.3 pounds per cubic foot (0.214 grams per cubic cm), such as is available from Fulflex Inc., of Middletown, R.I., or as available from Ludlow Composites Corporation of Freemont, Ohio and marketed under the tradename Baby Foam; or b) polyurethane foams having a caliper of approximately 80 mils and a density of approximately 2.06 pounds per cubic foot (0.033 grams per cubic cm), such as is available from Bridgestone of Yokohama, Japan and marketed under the tradename Bridgestone SG Polyurethane Foam. Other suitable materials for use as or in the belt flaps include structural elastic-like film (SELF) webs, as described above, natural rubber, natural rubber foams, elastomeric scrims, woven or nonwoven elastomeric webs, elastomeric composites such as elastomeric nonwoven laminates, zero strain stretch laminates, prestrained stretch laminates or the like. The above referenced U.S. Pat. No. 5,151,092 issued to Buell et al., on Sep. 29, 1992, describes suitable zero strain stretch laminates and prestrained stretch laminates, and is herein incorporated by reference.

Figure 5:
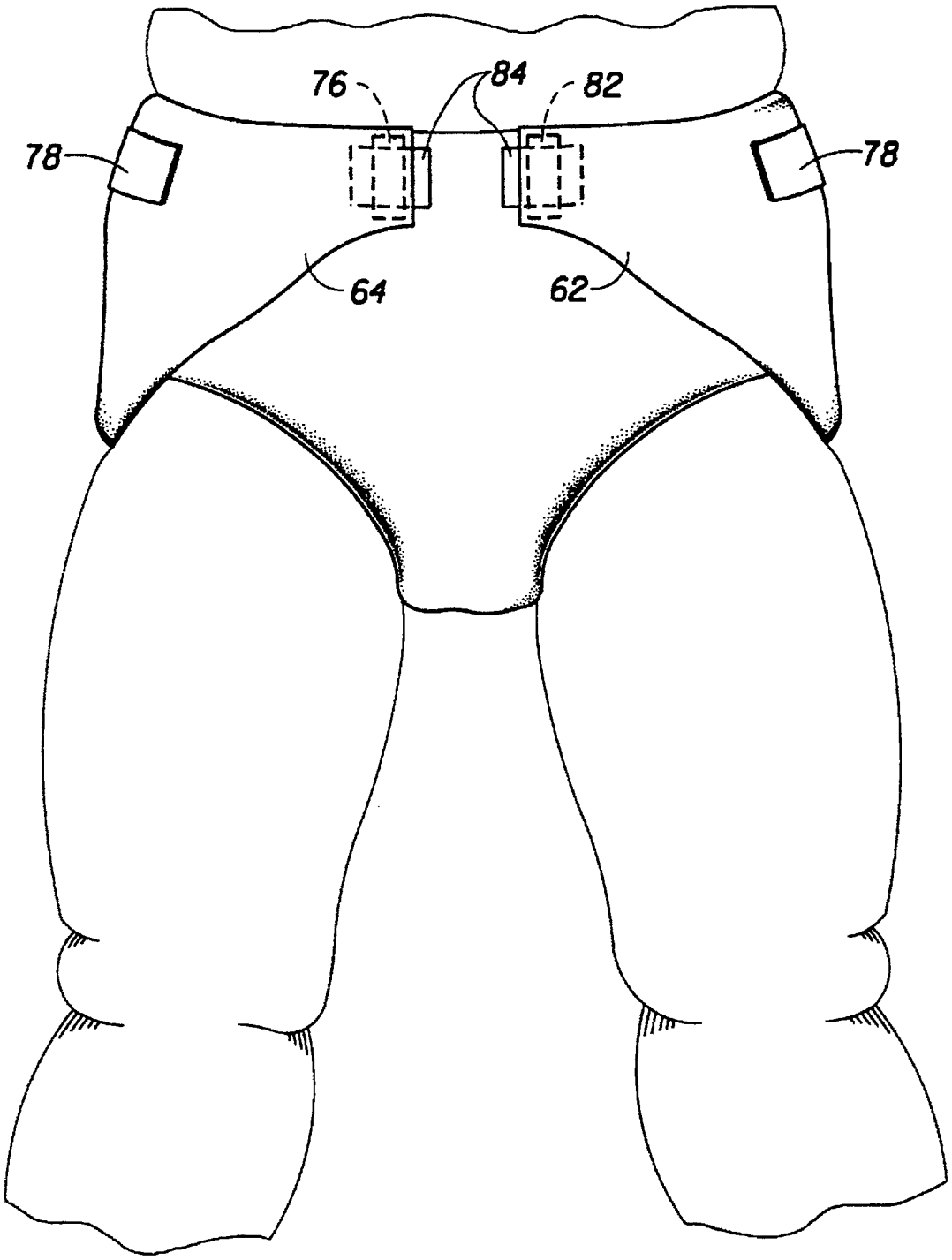
FIG. 5 is a front elevational view of the diaper fitted onto the wearer in the conventional configuration.

The diaper 20 additionally comprises a fastening system comprising a first fastening assembly and a second fastening assembly. The fastening system permits the user to construct and fit the diaper 20 to the wearer in at least two different configurations (i.e., the diaper is convertible). The first fastening assembly is designed to fasten the diaper 20 in a belted configuration. As used herein, the term "belted configuration" refers to a diaper that is fitted to the wearer by first constructing a belt about the waist of the wearer and then completing the application by forming a closure between the front and rear portions of the diaper. (The term "belt" means any element or elements of the diaper that fasten together to completely encircle the waist of the wearer prior to forming the closure between the front and rear portions of the diaper.) The second fastening assembly is designed to fasten the diaper 20 in a conventional configuration. The term "conventional configuration" refers to a diaper that is fitted to the wearer without the construction of a belt as described above. As shown in FIG. 5, a preferred embodiment of the present invention constructed in the conventional configuration is fitted to the wearer by placing the rear waist region 44 of the diaper 20 under the back of the wearer, pulling the front waist region 46 through the legs of the wearer to the wearer's waist and fastening the front waist region 46 to the waist region 44 to form side closures and to complete construction of the diaper 20.

In preferred embodiments of the present invention, the fastening system is designed such that the soft, non-irritating elements of the diaper and the fastening assemblies will come in contact with the wearer's skin. Further, the fastening assemblies are preferably integrated to reduce the number of fastening elements needed to achieve the convertible diaper design. (As used herein, the term "integrated" refers to the coordination of the fastening assemblies such that one or more of the individual fastening elements used in the first fastening assembly is also used in the second fastening assembly.) This integration reduces the cost of the material needed in the fastening system thus reducing the overall manufacturing cost of the diaper 20.

The fastening system can comprise any attachment means known in the art including pressure sensitive adhesives, cohesive materials, mechanical fasteners, such as hook and loop type fasteners, or any combination of these or any other attachment means known in the art. Exemplary adhesive tape tab fastening systems are disclosed in U.S. Pat. No. 3,848,594 entitled "Tape Fastening System for Disposable Diaper" issued to Buell on Nov. 19, 1974; and U.S. Pat. No. 4,662,875 entitled "Absorbent Article" issued to Hirotsu and Robertson on May 5, 1987. Exemplary fastening systems comprising mechanical fastening components are described in U.S. Pat. No. 5,058,247 entitled "Mechanical Fastening Prong" issued to Thomas on Oct. 22, 1991; U.S. Pat. No. 4,869,724 entitled "Mechanical Fastening Systems With Adhesive Tape Disposal Means For Disposal of Absorbent Articles" issued to Scripps on Sep. 26, 1989; and U.S. Pat. No. 4,848,815 entitled "Disposable Diaper Having an Improved Fastening Device" issued to Scripps on Jul. 11, 1989. An example of a fastening system having combination mechanical/adhesive fasteners is described in U.S. Pat. No. 4,946,527 entitled "Pressure-Sensitive Adhesive Fastener and Method of Making Same" issued to Battrell on Aug. 7, 1990. Each of these patents are incorporated herein by reference.

In a preferred embodiment of the present invention, the fastening system comprises hook and loop type fasteners. As used herein, the term "hook and loop type fasteners" refers to fastening means comprising a "hook" component (hereinafter refered to as an "engaging component") and a complementary loop component (hereinafter refered to as a "landing component"). The term "hook" is used to designate a material having engaging elements. Thus, the hook fastening material may also be referred to as a male fastener. It should also be understood that the use of the term "hook" should be non-limiting in the sense that the engaging elements may comprise any shapes as are known in the art so long as they are adapted to engage a complementary landing component.

One embodiment of the present invention comprises a hook fastening material preferably comprising a base and a plurality of engaging elements extending from the base. The hook fastening material is intended to engage fibrous elements of a loop fastening material so as to provide a secure fastening device. Thus, the hook fastening material may be manufactured from a wide range of materials. Suitable materials include nylon, polyester, polypropylene, or any combination of these materials. A suitable hook fastening material comprises a number of shaped engaging elements projecting from a woven backing such as the commercially available material designated "SCOTCHMATE" brand No. FJ3402 available from Minnesota Mining and Manufacturing Company, St. Paul, Minn. Alternatively, the engaging elements may have any shape such as hooks, "T's" or any other shape as are well known in the art. A particularly preferred hook fastening material is described in U.S. Pat. No. 5,058,247 entitled "Mechanical Fastening Prong" issued to Thomas Oct. 22, 1991 which is incorporated herein by reference.

The landing component preferably comprises a fastening element engageable with the hook component. Thus, the landing component may be manufactured from a wide range of materials and configurations capable of securely engaging the hook component. For example, the landing component may comprise identical complementary elements or distinct complementary elements. As used herein, the term "identical complementary elements" is used to define mechanical fastening systems wherein the engaging elements of the hook component and the landing component comprise the same configuration or structure that are interlocking. Examples of such systems are described in Brown et al. U.S. Pat. No. 4,322,875 entitled "Two Strip Materials Used For Forming Fasteners" issued on Apr. 16, 1982 and Kellenberger et al. U.S. Pat. No. 4,701,179 entitled "Fixed Position Fasteners For Disposable Absorbent Garments" issued on Oct. 20, 1987. The term "distinct complementary elements" is used herein to designate a system wherein the hook component is different from the landing component but is engageable therewith.

In one preferred embodiment, the landing component comprises a plurality of fiber elements, such as a loop fastening material, that engage the engaging elements of the hook component. The loop fastening material may be manufactured from a wide range of materials to provide fiber elements, preferably loops. Suitable materials include nylon, polyester, polypropylene, or any combination of these materials. A suitable loop fastening material comprises a number of fiber loops projecting from a woven backing such as the commercially available material designated "SCOTCHMATE" brand nylon woven loop No. SJ3401 available from Minnesota Mining and Manufacturing Company, St. Paul, Minn. A preferred loop fastening material comprises a tricot knit fabric having a plurality of nylon filament loops projecting from a backing of nylon such as the commercially available material designated "Guilford No. 16110" available from Guilford Mills of Greensboro, N.C. Alternatively, the loop fastening material may be a non-woven fabric or any other type of fiber material or loop material which are well known in the art. An inexpensive loop fastening material and a method of making the same is described in U.S. Pat. No. 5,032,122, entitled "Loop Fastening Material For Fastening Device and Method of Making Same" issued to Noel et al., Jul. 16, 1991, which application is incorporated herein by reference.

The fastening elements may be disposed on either the outer surface or the inner surface of the diaper 20. In a preferred embodiment, however, the fastening elements are disposed on the diaper 20 such that the fasteners do not irritate the wearer's skin. Accordingly, the fasteners disposed on inner surfaces of the diaper 20 that come in contact with the wearer's skin should be soft and non-irritating. In addition, the fastening elements may either be a discrete separate element affixed to the diaper 20 or a unitary piece of material that is neither divided nor discontinuous with an element of the diaper 20 such as the topsheet 24 or the backsheet 26. While the fastening elements can assume varying sizes and shapes, they preferably comprise one or more separate patches of material joined to the diaper 20 to allow for a maximum fit adjustment at the waist of the wearer.

As shown in FIGS. 1 and 2, the first fastening assembly of the present invention comprises a first belt flap closure member 74, a second belt flap closure member 76, a rear waist region closure member 78 and a second front waist region closure member 80. The first belt flap closure member 74 preferably comprises an engaging component and is preferably disposed adjacent the first belt flap's distal edge 68 on the outer surface 69 such that the fastening surface faces away from the wearer. (As used herein, the term "fastening surface" refers to the surface of a fastening element that is engageable with the fastening surface of another fastening element or any other surface of any element of the diaper.) The first belt flap closure member 74 may either be a discrete separate element affixed to the diaper 20 or a unitary piece of material that is neither divided nor discontinuous with an element of the diaper 20. When constructing the diaper 20 in the belted configuration, the first belt flap closure member 74 is engaged with the second belt flap closure member 76 to form a belt about the waist of the wearer.

The second belt flap closure member 76 preferably comprises a landing component and is preferably disposed adjacent the second belt flap's distal edge 72, on the inner surface 67 such that the fastening surface faces the wearer. The second belt flap closure member 76 may either be a discrete separate element affixed to the diaper 20 or a unitary piece of material that is neither divided nor discontinuous with an element of the diaper 20 such as the topsheet 24. When constructing the diaper 20 in the belted configuration, the second flap closure member 76 is engaged with the first belt flap closure member 74 to form a belt about the waist of the wearer. When the diaper 20 is constructed in the conventional configuration, the second belt flap closure member 76 engages the third closure member 84 to fasten the rear waist region 44 to the front waist region 46.

The rear waist region closure member 78 preferably comprises an engaging component and is preferably disposed on the outer surface 69 of the rear waist region such that the fastening surface faces away from the wearer. The rear waist closure member 78 may either be a discrete separate element affixed to the diaper 20 or a unitary piece of material that is neither divided nor discontinuous with the elements of the diaper 20 forming the rear waist region 44 of the diaper 20, such as the backsheet 26. Further, the rear waist closure member 78 can assume varying sizes and shapes, preferably one or more separate patches of material joined to the diaper 20 to allow for a maximum fit adjustment at the waist of the wearer. When the diaper 20 is constructed in the belted configuration, the front waist region closure member 80 engages the rear waist region closure members 78 to secure the front waist region 46 of the diaper 20 to the rear waist region 44.

The front waist region closure member 80 preferably comprises at least one landing component disposed adjacent each longitudinal edge 50 of the containment assembly 22 in the front waist region 46. In embodiments of the present invention comprising ear flaps 38, the front waist region closure member 80 comprises at least one closure member disposed on each of the ear flaps 38, preferably laterally outboard from the longitudinal edges 50 of the containment assembly. The front waist region closure member 80 is preferably a discrete separate element disposed on the outer surface 40 of the diaper 20 such that the fastening surface faces the wearer. However, embodiments are contemplated wherein the front waist region closure member 80 is unitary with the ear flaps 38 or other elements of the diaper 20, such as the topsheet 24. Further, the front waist region closure member 80 may be disposed on the inner surface 42 of the diaper such that the fastening surface faces the wearer. When the diaper is constructed in the belted configuration, the front waist region closure members 80 engages the rear waist region closure members 78 to secure the front waist region 46 of the diaper 20 to the rear waist region 44. In the conventional configuration, however, at least a portion of each front waist region closure member 80 is positioned against the wearer's skin. Therefore, it is important that the portion of the front waist region closure members 80 that will come in contact with the wearer's skin comprise a soft, non-irritating material.

As shown in FIGS. 1 and 2, the second fastening assembly comprises a first closure member 82, the second belt flap closure member 76 of the first fastening assembly, and a third closure member 84. The first closure member 82 preferably comprises a landing component and is preferably disposed adjacent the first belt flap's distal edge 68, on the inner surface 67 such that the fastening surface faces the wearer. The first closure member 82 may either be a discrete separate element affixed to the diaper 20 or a unitary piece of material that is neither divided nor discontinuous with an element of the diaper 20 such as the topsheet 24. When the diaper 20 is constructed in the conventional configuration, the first closure member 82 engages the third closure member 84 to secure the rear waist region 44 of the diaper 20 to the front waist region 46. However, when the diaper 20 is constructed in the belted configuration, at least a portion of the first closure member 82 contacts the skin of the wearer. Therefore, it is important that the portion of the first closure members 82 that will come in contact with the wearer's skin comprise a soft, non-irritationg material.

The second belt flap closure member 76 preferably comprises a landing component and is preferably disposed adjacent the second belt flap's distal edge 72, on the inner surface 67 such that the fastening surface faces the wearer. (The second belt flap closure member 76 is described in more detail above with respect to the first fastening assembly).

The third closure member 84 preferably comprises an engaging component and is preferably disposed adjacent the end edge 52 of the diaper 20, in the front waist region 46. The third closure member is preferably disposed on the outer surface 40 of the diaper 20 such that the fastening surface faces away from the wearer. The third closure member 84 may comprise either a discrete separate element affixed to the diaper 20 or a unitary piece of material that is neither divided nor discontinuous with an element of the diaper 20 such as the backsheet 26. Further, the third closure member 84 can assume varying sizes and shapes, they preferably comprises one or more separate patches of material joined to the diaper 20 to allow for a maximum fit adjustment at the waist of the wearer. When the diaper 20 is constructed in the conventional configuration, the third closure member 84 engages the first closure member 82 and the second belt flap closure member 76 to secure the front waist region 46 of the diaper 20 to the rear waist region 44.

In a preferred embodiment, the present invention provides the diaperer with at least three options as to how the diaper may be constructed and fit to the wearer. If the diaperer prefers to use the belted diaper configuration, the diaper 20 is preferably constructed and applied to the wearer using the first fastening assembly. Preferably, the diaper is first positioned such that the rear waist region 44 is behind the hips of the wearer with the from waist region 46 extends toward the wearer's legs. This positions the diaper 20 such that first belt flap 62 and the second belt flap 64 can be fastened together to form a belt about the waist of the wearer. To construct the belt, the diaperer engages the first belt flap closure member 74 disposed on the outer surface 69 of the first belt flap 62 with the second belt flap closure member 76 disposed on the inner surface 67 of the second belt flap 64. The diaperer then pulls the front waist region 46 of the diaper 20 through the wearer's legs and up to the wearer's waist. Once in this position, the front waist region 46 of the diaper 20 can be fastened to the rear waist region 44 of the diaper 20. The side closures are formed by engaging the front waist region fastening members 80, disposed on the inner surface 42 of the front waist region 46 adjacent each longitudinal edge 50 of the containment assembly 22, with the rear waist region closure member 78 disposed on the outer surface 40 of the containment assembly 22 in the rear waist region 44.

If the diaperer wishes to use the diaper in the conventional configuration, the second fastening assembly is used. The diaper 20 is preferably applied to the wearer in the conventional configuration by first positioning one of the waist regions, preferably the rear waist region 44, under the wearer's back. The remainder of the diaper 20 is then drawn between the wearer's legs such that the other waist region, preferably the front waist region 46, is positioned across the front of the wearer. The diaperer then grasps the first belt flap 62 or the second belt flap 64, or both and wraps them around the waist of the wearer. The diaperer then engages the first closure member 82 disposed on the inner surface 67 of the first belt flap 62 and the second belt flap closure member 76 disposed on the inner surface 67 of the second belt flap 64 with the third closure member 84 disposed on the outer surface 40 of the containment assembly 22 in the front waist region 46. This forms a waist closure on each side of the wearer and completes the construction of the conventional diaper using the second fastening assembly.

In a particularly preferred embodiment of the present invention, the diaper can be used as a pant. For example, the diaper can be constructed in either the conventional or the belted configuration to form a pant before fitting the diaper to the wearer. The diaperer or wearer then pulls the diaper up and over the wearer's hips where it is held in place around the wearer's waist by the inward forces provided by the elastic waist feature. In this configuration, the diaper can be removed by pulling the diaper down and off the wearer without releasing the fastening system, or by releasing the fastening system and removing the diaper from around the wearer's waist. Alternatively, the diaper can be constructed and fit to the wearer as herein described with respect to the conventional or the belted diaper configurations and be removed by pulling the diaper down over the wearer's hips and off the wearer without releasing the fastening system. Accordingly, the diaperer is provided with additional options as to how the diaper will be fitted to and/or removed from the wearer. This type of diaper is particularly attractive as a training pant because it combines the feel of a pant with the advantages discussed herein with respect to ease of inspection for soiling and removal by releasing the fastening system.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a refastenable fastening system allowing the absorbent article to be fitted to a wearer in a belted configuration or in a conventional configuration, the absorbent article comprising:

a) a containment assembly having a rear waist region, a crotch section, a front waist region, a pair of longitudinal edges, an inner surface and an outer surface opposite of said inner surface, said containment assembly comprising a liquid pervious topsheet, a liquid impervious backsheet joined to said topsheet, and an absorbent core positioned between said topsheet and said backsheet;

b) a first belt flap extending laterally outwardly from one of said longitudinal edges of said containment assembly in said rear waist region, said first belt flap having a proximal edge joined to said rear waist region, a distal edge spaced laterally outwardly from said proximal edge, an inner surface, and an outer surface;

c) a second belt flap extending laterally outwardly from the other of said longitudinal edges of said containment assembly in said rear waist region, said second belt flap having a proximal edge joined to said rear waist region, a distal edge spaced laterally outwardly from said proximal edge, an inner surface, and an outer surface;

d) a first fastening assembly for fastening said absorbent article in a belted configuration comprising:

i) a first belt flap closure member disposed adjacent said distal edge on said first belt flap on said outer surface;

ii) a second belt flap closure member disposed adjacent said distal edge on said second belt flap on said inner surface, said second belt flap closure member being engageable with said first belt flap closure member to form a belt;

iii) a rear waist region closure member disposed on said outer surface on said containment assembly in said rear waist region; and iv) a front waist region closure member disposed adjacent each said longitudinal edge of said containment assembly in said front waist region on said inner surface; said front waist region closure member being engageable with said rear waist region closure member; and e) a second fastening assembly for fastening said absorbent article in a conventional configuration comprising:

i) a first closure member disposed adjacent said distal edge on said first belt flap on said inner surface, ii) said second belt flap closure member disposed adjacent said inner surface on said second belt flap adjacent said distal edge of said second belt flap, and iii) a third closure member disposed adjacent the end edge of said front waist region on said outer surface of said containment assembly, said third closure member being engageable with said second belt flap closure member component and said first closure member.

2. The absorbent article of claim 1 wherein said first fastening assembly comprises mechanical fasteners.

3. The absorbent article of claim 1 wherein said second fastening assembly comprises mechanical fasteners.

4. The absorbent article of claim 1 wherein said first fastening assembly and said second fastening assembly each comprise mechanical fasteners.

5. The absorbent article of claim 4 wherein said front waist region closure member, said first closure member and said second belt flap closure member comprise a landing component.

6. The absorbent article of claim 5 wherein said landing component comprises a loop component of a hook and loop fastener.

7. The absorbent article of claim 6 wherein said first belt flap closure member, said rear waist region closure member, and said third closure member comprise an engaging component.

8. The absorbent article of claim 7 wherein said engaging component comprises a hook component of a hook and loop fastener.

9. The absorbent article of claim 8 wherein said belt flaps are elastically extensible.

10. The absorbent article of claim 9 wherein said first and second belt flaps are unitary with said containment assembly.

11. The absorbent article of claim 9 wherein said first and second belt flaps are separate elements joined to said containment assembly.

12. The absorbent article of claim 1 wherein said first fastening assembly comprises adhesive fasteners.

13. The absorbent article of claim 1 wherein said second fastening assembly comprises adhesive fasteners.

14. The absorbent article of claim 1 wherein said first fastening assembly and said second fastening assembly comprise adhesive fasteners.

15. The absorbent article of claim 1 wherein said rear waist region closure member comprises a pair of fastening elements disposed on laterally opposing sides of the containment assembly.

* * * * *